United States Patent [19]

Kienzle et al.

[11] 3,975,445

[45] Aug. 17, 1976

[54] NOVEL POLYENE COMPOUNDS AND PROCESS THEREFOR

[75] Inventors: Frank Kienzle, Therwil; Hans Johann Mayer, Fullinsdorf, both of Switzerland

[73] Assignee: Hoffmann-La Roche Inc., Nutley, N.J.

[22] Filed: June 9, 1975

[21] Appl. No.: 585,219

[30] Foreign Application Priority Data

June 20, 1974 Switzerland.................. 8457/74

[52] U.S. Cl................. 260/590 C; 260/586 C; 260/617 A; 260/617 B; 260/593 R; 260/601 R; 260/606.5 P; 260/515 R; 260/526 R; 424/332; 424/244; 424/268

[51] Int. Cl.²............................................ C07C 49/76

[58] Field of Search........ 260/590 C, 586 C, 526 R, 260/590 D, 606.5 F, 515 R

[56] References Cited

UNITED STATES PATENTS

| | | | |
|---|---|---|---|
| 3,429,928 | 2/1969 | Surmatis et al. | 260/586 C |
| 3,466,331 | 9/1969 | Surmatis et al. | 260/586 C |
| 3,781,314 | 12/1973 | Bollag et al. | 260/586 C |

*Primary Examiner*—James O. Thomas, Jr.
*Assistant Examiner*—James H. Reamer
*Attorney, Agent, or Firm*—Samuel L. Welt; Bernard S. Leon; Richard A. Gaither

[57] ABSTRACT

A novel process for the preparation of polyene compounds useful as coloring agents in foods, cosmetics, and pharmaceutical preparations. Novel polyenes are also disclosed.

The present invention relates to polyene compounds. More particularly, the invention is concerned with novel carotenoid polyene compounds, derivatives thereof and a process for their manufacture.

4 Claims, No Drawings

NOVEL POLYENE COMPOUNDS AND PROCESS THEREFOR

BACKGROUND OF THE INVENTION

The use of carotenoids as coloring agents in foods, cosmetics, and pharmaceuticals is a common occurence. The search continues, however, for new compounds in the carotenoid class which require smaller amounts of the material to impart a high degree of color intensity to the material to be colored. Such a compound is di-nor-canthaxanthin and derivatives thereof. However, according to procedures known heretofore, these compounds are producible only in very low yields which are non-commercially feasible.

It is an object therefore of this invention to produce di-nor-canthaxanthin and derivatives therefore in commercially feasible quantities.

SUMMARY OF THE INVENTION

In one of its aspects, the invention is concerned with the polyene compound of the formula:

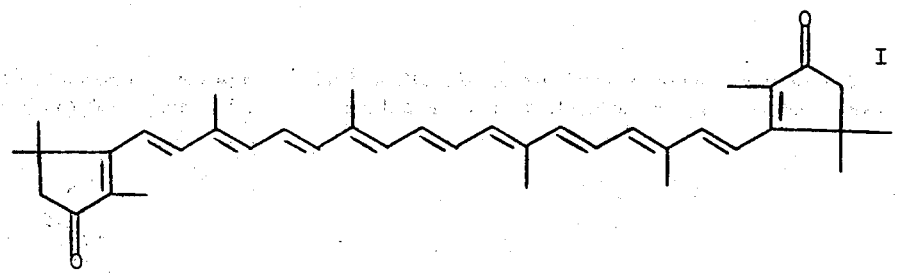

which is referred to hereinafter as di-nor-canthaxanthin.

In another aspect, the invention is concerned with di-nor-isozeaxanthin of the formula:

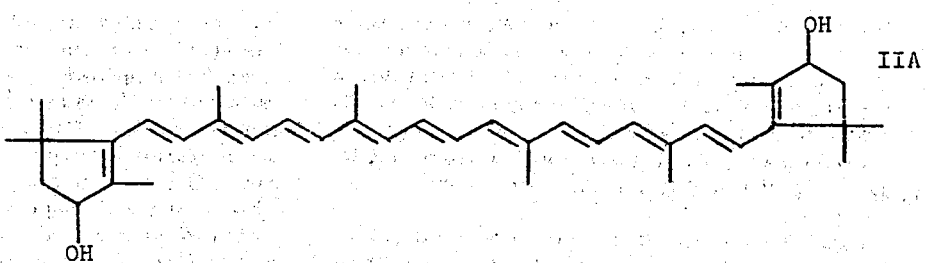

which can be obtained by reducing di-nor-canthaxanthin.

Di-nor-canthaxanthin of formula I can be converted by oxidation into di-nor-astacin [violerythrin] of the formula:

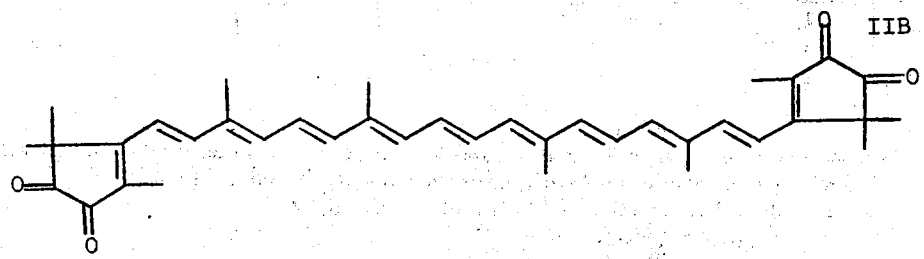

which can be reduced in a first reduction step to give di-nor-astaxanthin [actinioerythrol] of the formula:

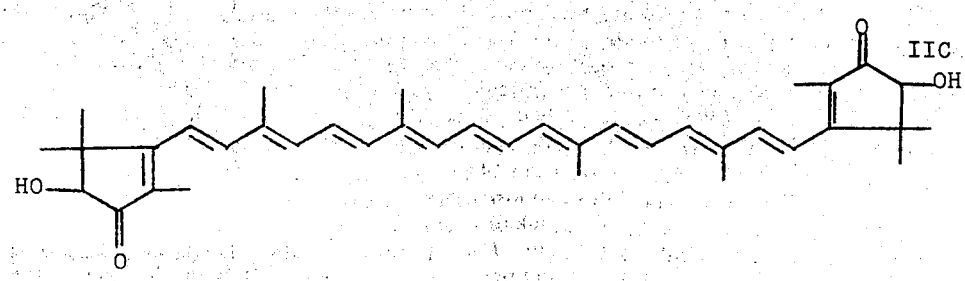

and in a second reduction step to give di-nor-crustaxanthin [violerythrol] of the formula:

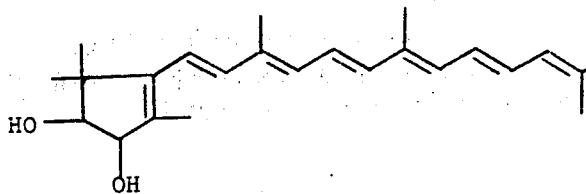

The polyene compounds of formula IIB, IIC and IID hereinbefore can be generically depicted as follows:

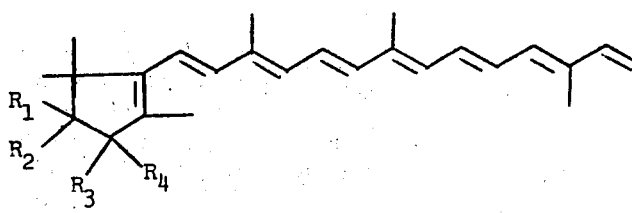

wherein one of the paiir of $R_1$, and $R_2$, $R_5$ and $R_6$ is hydroxy and the other is hydrogen and one of the pair of $R_3$ and $R_4$, $R_7$ and $R_8$ is hydroxy and the other is hydrogen or $R_3$ and $R_4$ taken together and $R_7$ and $R_8$ taken together are an oxo group; or $R_1$ and $R_2$ taken together and $R_5$ and $R_6$ taken together and $R_3$ and $R_4$ taken together and $R_7$ and $R_8$ taken together are an oxo group.

The polyene compounds of formulae I and IIA hereinbefore are novel and form part of this invention. They can be generically formulated as follows:

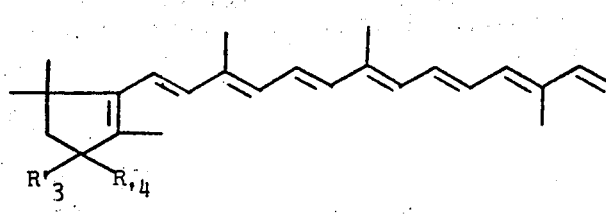

wherein one of the pair of $R'_3$ and $R'_4$ and $R'_7$ and $R'_8$ is hydroxy and the other is hydrogen or the smybols $R'_3$ and $R'_4$ taken together and $R'_7$ and $R'_8$ taken together are an oxo group.

DETAILED DESCRIPTION OF THE INVENTION

As used herein, the term "alkyl" denotes straight or branched hydrocarbons having from 1 to 20 carbon atoms. Typical groups are methyl, ethyl, propyl, isopropyl, butyl, undecyl, dodecyl and the like. The term "lower alkyl" denotes hydrocarbon, as defined above, having from 1-6 carbon atoms. The term "halo" as used herein, denotes the four halogens, fluorine, chlorine, bromine and iodine. The term "alkali metal", denotes sodium, potassium, and lithium. The term "mineral acid", denotes sulfuric, nitric and phosphoric acids. The term hydrohalic acid, as used herein, denotes hydrofluoric, hydrochloric, hydrobromic and hydroidic acids. The term "aryl" as used herein, denotes mononuclear aryl groups such as phenyl, tolyl, ethylbenzyl and the like and polynuclear aryl groups

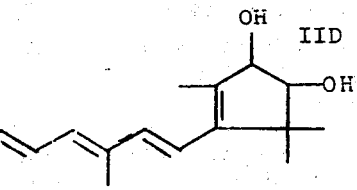

such as naphthyl, anthryl, phenanthryl and the like. The term "lower alkylene", as used herein, denotes straight or branched alkylene groups having from 1–6 carbon atoms, such as methylene, ethylene, isopropylene and the like. The term "lower alkanol", as used herein, denotes straight or branched chain alkanols having from 1 to 6 carbon atoms such as methanol, ethanol, propanol, isopropanol and the like.

The process provided by the present invention for the manufacture of di-nor-canthaxanthin comprises (i) condensing, with an organo-phosphorus compound as

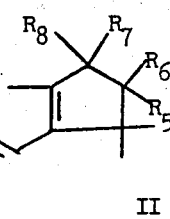

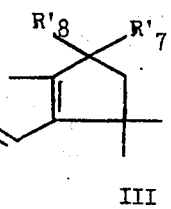

condensing agents, an aldehyde or halide of the formula:

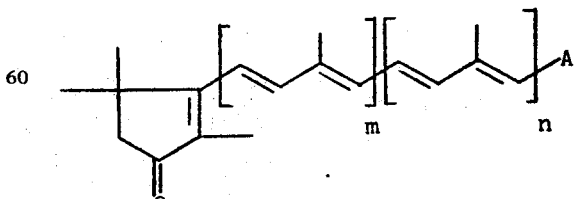

IV with a halide or aldehyde of the formula:

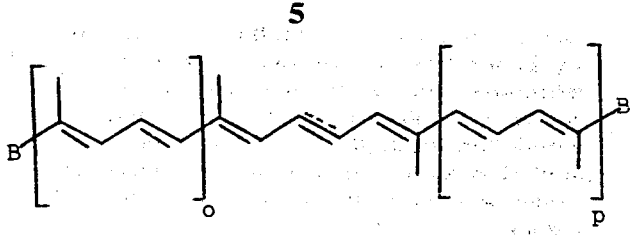

in which formulae one of A and B is the formyl group and the other is a halomethyl group and wherein the broken line denotes an optional carbon-carbon bond; said condensation being carried out by reacting an aldehyde or halide of formula IV in which $m$ and $n$ are both zero and a halide or aldehyde of formula V in which $o$ and $p$ are both 1, or an aldehyde or halide of formula IV in which $m$ is 1 and $n$ is zero and a halide or aldehyde of formula V in which $o$ and $p$ are both zero;

or (ii) condensing, with an organo-phosphorus compound as condensing agent, a compound of formula IV in which $m$ and $n$ are both 1 and A is the formyl group with a second paragraph of formula IVA in which $m'$ and $n'$ are both 1 and $A'$ is a halomethyl group, said second compound having the formula:

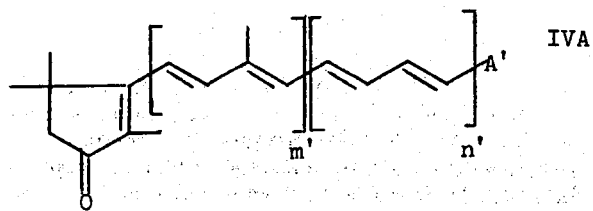

IVA and (iii) hydrogenating any triple bond present in the product obtained to a double bond.

Of the aforementioned organo-phosphorus condensation reactions used in the manufacture of di-nor-canthaxanthin of formula I, the Wittig reaction is preferred. Such a reaction is advantageously carried out by condensing a compound of the formula:

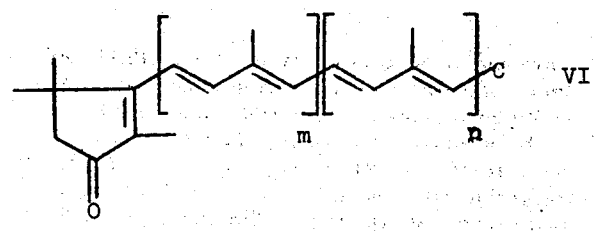

VI with a compound of the formula:

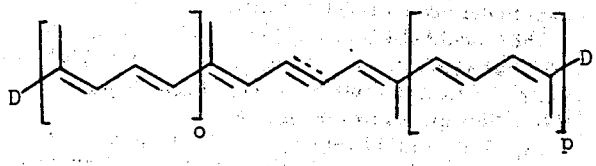

VII wherein the symbols $m$, $n$, $o$ and $p$ and the broken line are as previously defined and one of C and D repre-

sents the formyl group and the other is a triarylphosphoniummethyl group of the formula:

$-CH_2-P[X]_3^+ \ Y^-\cdot$ wherein X is an aryl group and Y is an anion of an acid selected from the group consisting of $Cl^-$, $Br^-$, $SO_4^=$, $R_9COO^-$, wherein $R_9$ is lower alkyl or phenyl;

or by condensing a compound of formula VI which is oxo substituted and where $m$ and $n$ are both 1 with a second compound of formula VI which is substituted by a triarylphosphoniummethyl group and where $m$ and $n$ are both 1.

The Wittig reagents that may be employed are the well known phosphonium compounds. Typical Wittig reagents used herein are triphenyl phosphonium chloride, triphenylphosphonium bromide, tributylphosphonium chloride or bromide, tribenzyl phosphonium chloride or bromide. Mixed aryl and alkyl phosphonium halides may be employed as well.

Of the aforementioned procedures for the manufacture of di-nor-canthaxanthin of formula I, the following procedures denoted as (a), (b), (c) and (d) have been found to be especially advantageous:

a. the condensation of a compound of the formula:

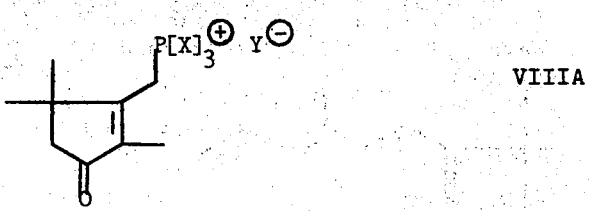

VIIIA wherein X and Y are as previously defined; with a compound of the formula:

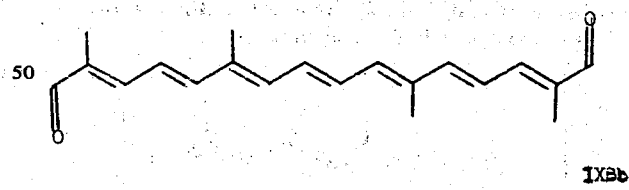

IXBb b. the condensation of a compound of the formula:

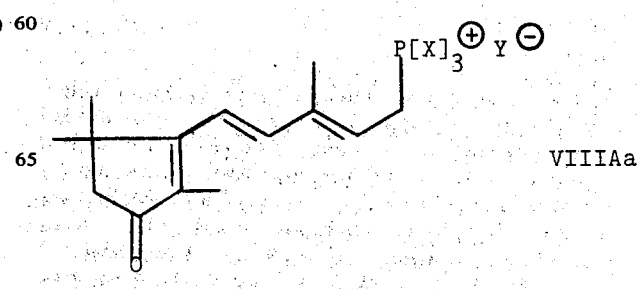

VIIIAa wherein X and Y are as previously defined;
with a compound of the formula:

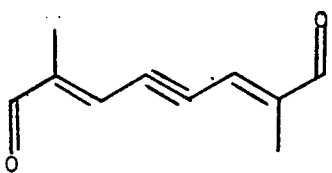 IXB c. the condensation of a compound of the formula:

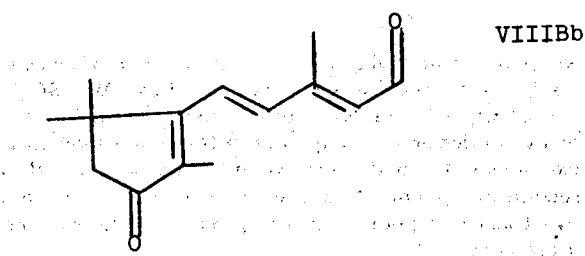 VIIIBb with a compound of the formula:

$P[X]_3^{\oplus} \ Y^{\ominus}$  IXA

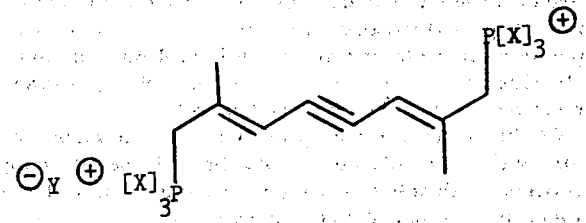

wherein X and Y are as previously defined, d. the condensation of a compound of the formula:

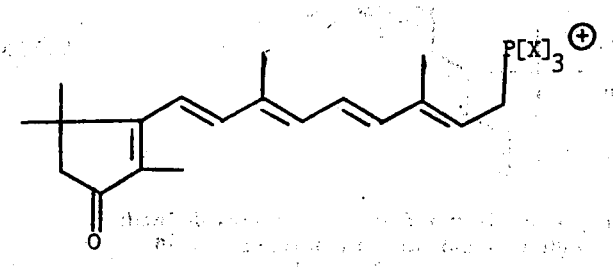

wherein X and Y are as previously defined above;
with a compound of the formula:

$P[X]_3^{\oplus} \ Y^{\ominus}$  VIIIAaa

VIIIBbb

The condensation components are reacted according to the Wittig procedure in the presence of an acid-binding agent such as an alkali metal hydroxide such as sodium hydroxide, lithium hydroxide, potassium hydroxide or an alkali metal lower alkyl alcoholate potassium ethylate, sodium methylate and the like or lower alkylene oxide which may be lower alkyl-substituted, especially ethylene oxide or butylene oxide, in the presence or absence of a solvent. If a solvent is employed, any inert solvent such as lower alkanols, chlorinated hydrocarbon such as methylene chloride, carbon tetrachloride, chlorobenzene and the like. Amides such as dimethylformamide (DMF) tetramethylurea and hexamethylphosphoric acid triamide at a temperature between room temperature and the boiling point of the mixture.

Di-nor-canthaxanthin of formula I, which is novel, is a cherry-red colored substance and the novel di-nor-isozeaxanthin of formula IIA obtainable therefrom by reduction is an intensively orange-red colored substance.

Di-nor-astacin [violerythrin] of formula IIB, a known compound obtainable from di-nor-canthaxanthin of formula I by oxidation, has a deep-blue color, the red di-nor-astaxanthin [actinioerythrol] of formula IIC, obtainable from di-nor-astacin by reduction, is also known as is the orange-colored di-nor-crustaxanthin [violerythrol] of formula IID which is obtainable from IIC by reduction.

Violerythrin of formula IIB has previously been produced in micro amounts starting from actinioerythriin [actinioerythrol diester], a coloring material isolated from sea-anemones, by saponification to actinioerythrol and subsequent oxidation. Violerythrin can also be obtained in a semi-synthetic manner by the ring-contraction of astacin, the yield being only about 10%.

The process in accordance with the present invention now provides a technically feasible approach to the foregoing coloring substances which are eminently suitable for the coloring and improving of, inter alia, foods and beverages.

The cyclopentyl derivatives used as the condensation components in procedures (a), (b), (c) and (d) hereinbefore are novel and can be prepared from novel starting materials via various methods.

The methyl-(3-oxo-2,5,5-trimethyl-cyclopent-1-en-1-yl)triarylphosphonium halide of formula VIIIA used in procedure (a) can be prepared according to any of the following known procedures:

$a_1$. 2,4,4-trimethyl-cyclopent-2-en-1-one is reacted with nitromethane to give 2,4,4-trimethyl-3-nitromethyl-cyclopentanone which, after treatment with a base, is converted into 1-formyl-3-oxo-2,5,5-trimethyl-cyclopentane either with the aid of an oxidizing agent, such as potassium permanganate, ozone, or with a hydrohalic acid, a mineral acid or titanium trichloride.

The aldehyde obtained is subsequently dehydrogenated with the aid of a dehydrogenating agent, such as 2,3-dichloro-5,6-dicyanobenzoquinone, sulfuryl chloride or selenium dioxide, to the corresponding 1-formyl-3-oxo-2,5,5-trimethylcyclopent-1-ene which is subsequently reduced to 1-hydroxymethyl-3-oxo-2,5,5-trimethyl-cyclopent-1-ene by treatment with a chemical reducing agent such as sodium or lithium aluminum hydride, sodium or lithium borohydride, lower alkyl aluminum hydrides such as diisobutylaluminum hydride, diethyl aluminum hydride and the like.

The alcohol obtained is then converted by treatment with a halogenating agent such as phosphorus pentachloride, phosphorus tribromide, thionyl chloride or phosgene phosphorus trichloride, into a 1-halomethyl-3-oxo-2,5,5-trimethyl-cyclopent-1-ene which is converted by reaction with a triarylphosphine (e.g. triphenylphosphine) into a methyl-(3-oxo-2,5,5-trimethyl-cyclopent-1-en-1-yl)-triarylphosphonium halide of formula VIIIA.

$a_2$. 1-Methoxycarbonyl-3-oxo-2,5,5-trimethyl-cyclopentane is reacted with ethanedithiol in the presence of boron trifluoride etherate to give 7-methoxycarbonyl-6,8,8-trimethyl-1,4-dithiaspiro[4,4]nonane which is reduced to 7-hydroxymethyl-6,8,8-trimethyl-1,4-dithia-spiro[4,4]nonane by treatment with a reducing agent. The reducing agents that may be employed may be selected from those mentioned hereinbefore.

The alcohol obtained is subsequently converted by treatment with desulfurizing agent [e.g cadmium carbonate and mercury (II) chloride] into 1-hydroxymethyl-3-oxo-2,5,5-trimethyl-cyclopentane which is oxidized to 1-formyl-3-oxo-2,5,5-trimethyl-cyclopentane by treatment with an oxidizing agent e.g. with chromium(III)oxide, manganese dioxide or silver(I)oxide. The aldehyde obtained is subsequently converted into a phosphonium salt of formula VIIA via the intermediate stage described in method ($a_1$) above.

$a_3$. 1-Carboxy-3-oxo-2,5,5-trimethyl-cyclopentane is first dehydrogenated and halogenated and subsequently esterified by treatment with thionyl chloride/sulphuryl chloride followed by the addition of methanol. The 1-methoxycarbonyl-3-oxo-2,5,5-trimethyl-cyclopent-1-ene obtained is then reduced with the aid of a reducing agent (e.g. sodium borohydride) firstly to 1-methoxycarbonyl-3-hydroxy-2,5,5-trimethyl-cyclopent-1-ene and subsequently with the aid of diisobutyl aluminum hydride to 1-hydroxymethyl-3-hydroxy-2,5,5-trimethyl-cyclopent-1-ene.

The diol obtained is oxidised to 1-formyl-3-oxo-2,5,5-trimethyl-cyclopent-1-ene by treatment with an oxidising agent [e.g. manganese dioxide, silver (I) oxide or nickel peroxide]. The aldehyde obtained is subsequently converted into a phosphonium salt of formula VIIA via the intermediate stage described in method ($a_1$) hereinbefore.

$a_4$. The 1-methoxycarbonyl-3-oxo-2,5,5-trimethyl-cyclopent-1-ene mentioned as the "building brick" in method ($a_3$) is reacted with ethanedithiol in the presence of boron trifluoride etherate to give 7-methoxycarbonyl-6,8,8-trimethyl-1,4-dithia-spiro[4,4]non-6-ene which is reduced to 7-hydroxymethyl-6,8,8-trimethyl-1,4-dithia-spiro[4,4]non-6-ene by treatment with a reducing agent (e.g. diisobutylaluminum hydride).

The alcohol obtained is subsequently converted into 1-hydroxymethyl-3-oxo-2,5,5-trimethyl-cyclopent-1-ene by treatment with a desulphurising agent [e.g. by the action of cadium carbonate and mercury (II) chloride].

The alcohol obtained is subsequently converted into a phosphonium salt of formula VIIIA via the intermediate stage previously described in method ($a_1$) hereinbefore.

A 5-(3-oxo-2,5,5-trimethyl-cyclopent-1-en-1-yl)-3-methylpenta-2,4-diene-1-triarylphosphonium halide of formula VIIIAa used in method (b) can be prepared in a manner known per se; for example, as follows:

$b_1$. A 1-halomethyl-3-oxo-2,5,5-trimethyl-cyclopent-1-ene used as the "building brick" in method ($a_1$) is reacted with a sulphinic acid or with an alkali salt thereof, preferably with an alkyl-sulphinic acid or an aryl-sulphinic acid in which the aryl group may carry one or more alkyl groups or one or more electron-repelling or weakly electron-attracting substituents.

The sulphone obtained, for example methyl-(3-oxo-2,5,5-trimethyl-cyclopent-1-en-1-yl)-phenylsulphone, is reacted with 1-acetoxy-4-chloro-3-methyl-but-2-ene to give 5-(3-oxo-2,5,5-trimethyl-cyclopent-1-en-1-yl)-5-phenylsulphonyl-3-methylpent 2-en-1-ol which is oxidised to the corresponding aldehyde by treatment with an oxidising agent [e.g. manganese dioxide or silver (I) oxide].

The sulphone group of the resulting 5-(3-oxo-2,5,5-trimethyl-cyclopent-1-en-1-yl)-5-phenylsulphonyl-3-methylpent 2-en-1-al is subsequently eliminated by the action of a basic agent, especially an alkali hydroxide, alcoholate or amide, to form an additional carbon-carbon bond.

The 5-(3-oxo-2,5,5-trimethyl-cyclopent-1-en-1-yl)-3-methyl-penta-2,4-dien-1-al of formula VIIIBb obtained is subsequently reduced to 5-(3-oxo-2,5,5-trimethyl-cyclopent-1-en-1-yl)-3-methyl-penta-2,4-dien-1-ol by treatment with a reducing agent (e.g. sodium borohydride) or by catalytic means.

The alcohol obtained is converted by treatment with a halogenating agent (e.g. phosphorus tribromide) into a 1-halo-5-(3-oxo-2,5,5-trimethylcyclopent-1-en-1-yl)-3-methyl-penta-2,4-diene which, by reaction with a triarylphosphine (e.g. triphenylphosphine) is converted into a 5-(3-oxo-2,5,5-trimethyl-cyclopent-1-en-1-yl)-3-methyl-penta-2,4-diene-1-triarylphosphonium halide of formula VIIIAa which is used in procedure (b).

The 5-(3-oxo-2,5,5-trimethyl-cyclopent-1-en-1-yl)-3-methyl-penta-2,4-dien-1-al of formula VIIIBb used in procedure (c) can be prepared according to any of the following known procedures.

$c_1$. The 1-formyl-3-oxo-2,5,5-trimethyl-cyclopentane mentioned in the method ($a_1$) is condensed with a 1,1-dialkoxy-3-methyl-but-2-ene-4-triarylphosphonium halide to give 5-(3-oxo-2,5,5-trimethyl-cyclopent-1-yl)-3-methyl-penta-2,4-dien-1-al.

The aldehyde obtained is immediately converted with the aid of a dehydrogenating agent (e.g. 2,3-dichloro-5,6-dicyano-1,4-benzoquinone, sulphuryl chloride or selenium dioxide) into 5-(3-oxo-2,5,5-trimethyl-cyclopent-1-en-1-yl)-3-methyl-penta-2,4-dien-1-al of formula VIIIBb which is used in procedure (c).

The compounds of formulae VIIIAaa and VIIIBbb used in procedure (d) can be prepared according to the following procedure:

The aldehyde required for carrying out procedure (d), namely all-trans 9-(3-oxo-2,5,5-trimethyl-cyclopent-1-en-1-yl)-3,7-dimethyl-nona-2,4,6,8-tetraen-1-al of formula VIIIBbb can be prepared according to the following procedure:

d₁. A 1-halomethyl-3-oxo-2,5,5-trimethyl-cyclopent-1-ene mentioned in method (b₁) is condensed with 8-(p-tolysulfonyl)-3,7-dimethyl-octa-2,4,6-trien-1-al to give 9-(3-oxo-2,5,5-trimethyl-cyclopent-1-en-1-yl)-3,7-dimethyl-nona-2,4,6,8-tetraen-1-al of formula VIIIBbb which is used in procedure (d).

The 8-(p-tolysulfonyl)-3,7-dimethyl-octa-2,4,6-trien-1-al, mentioned above, can be prepared in the following manner:

1-Ethoxycarbonyl-6-hydroxymethyl-2-methyl-hepta-1,3,5-triene is halogenated by treatment with a halogenating agent, selected from those mentioned above. The halide obtained is subsequently reacted with the sodium salt of p-toluenesulfinic acid.

The 1-ethoxycarbonyl-7-tolysulfonyl)-2,6-diimethyl-hepta-1,3,5-triene obtained is reduced to 1-hydroxymethyl-7-p-tolysulfonyl-2,6-dimethyl-hepta-1,3,5-triene with the aid of a reducing agent selected from those previously mentioned.

The alcohol obtained is then oxidized to 8-(p-tolyl-sulfonyl)-3,7-dimethyl-octa-2,4,6-trien-1-al by treatment with an oxidizing agent selected from those mentioned above.

The resulting aldehyde is subsequently condensed with a 1-halo-methyl-3-oxo-2,5,5-trimethyl-cyclopent-1-ene in the manner previously described.

d₂. 5-(3-2,5,5-Trimethyl-cyclopent-1-en-1-yl)-5-phenylsulfonyl-3-methyl-pent-2-en-1-ol previously mentioned in method (b₁) is converted by treatment with a halogenating agent selected from those mentioned above, into a 1-halo-5-(3-oxo-2,5,5-trimethyl-cyclopent-1-en-1-yl)-5-phenylsulfonyl-3-methyl-pent-2-ene which, by reaction with a triarylphosphine (e.g. triphenylphosphin), is converted into a 5-(3-oxo-2,5,5-trimethyl-cyclopent-1-en-1-yl)-5-phenylsulfonyl-3-methyl-pent-2-ene-1-triarylphosphonium halide.

The phosphonium salt obtained is subsequently condensed with 1-acetoxy-3-methyl-but-2-en-4-al to give 9-(3-oxo-2,5,5-trimethyl-cyclopent-1-en-1-yl)-3,7-dimethyl-nora-2,4,6,8-tetraen-1-ol which is converted by treatment with an oxidizing agent, selected from those previously set forth, into all-trans 9-(3-oxo-2,5,5-trimethyl-cyclopent-1-en-1-yl)-3,7-dimethyl-nonal-2,4,6,8-tetraen-1-al of formula VIIIBbb which is used in procedure (d).

d₃. 5-(3-oxo-2,5,5-Trimethyl-cyclopent-1-en-1-yl)-5-phenylsulfonyl-3-methyl-pent-2-en-1-al previously mentioned in (b₁) is reacted with a 1,1-dialkoxy-3-methyl-but-2-ene-4-triarylphosphonium halide to form directly all-trans 9-(3-oxo-2,5,5-trimethyl-cyclopent-1-en-1-yl)-3,7-dimethyl-nona-2,4,6,8-tetraen-1-al of formula VIIIBbb which is used in procedure (d).

d₄. 5-(3-oxo-2,5,5-Trimethyl-cyclopent-1-en-1-yl)-3-methyl-penta-2,4-dien-1-al of formula VIIIBb previously mentioned in method (b₁), is reacted with a 1,1-dialkoxy-3-methyl-but-2-ene-4-triarylphosphonium halide to form directly all-trans 9-(3-oxo-2,5,5-trimethyl-cyclopent-1-en-1-yl)-3,7-dimethyl-nona-2,4,6,8-tetraen-1-al of formula VIIIBbb which is used in procedure (d).

The phosphonium salt required for carrying out procedure (d), namely an all-trans 9-(3-oxo-2,5,5-trimethyl-cyclopent-1-en-1-yl)-3,7-dimethyl-nona-2,4,6,8-tetraene-1-triarylphosphonium halide of formula VIIIAaa, can be obtained in the following manner:

d₅. 9-(3-2,5,5-trimethyl-cyclopent-1-en-1-yl)-3,7-dimethyl-nona-2,4,6,8-tetraen-1-ol mentioned in method (d₂) is halogenated by treatment with a halogenating agent selected from those set forth above, and subsequently converted by reaction with a triarylphosphine (e.g. triphenylphosphine) into a 9-(3-oxo-2,5,5-trimethyl-cyclopent-1-en-1-yl)-3,7-dimethyl-nona-2,4,6,8-tetraene-1-triarylphosphonium halide of formula VIIIAaa which is used in procedure (d).

d₆. The aforementioned phosphonium salt of formula VIIIAaa required for procedure d) can also be prepared starting from the aldehyde of formula VIIIBbb as follows: all-trans 9-(3-oxo-2,5,5-trimethyl-cyclohex-1-en-1-yl)-3,7-dimethyl-nona-2,4,6,8-tetraen-1-al is converted by treatment with a reducing agent, selected from those previously set forth, into 9-(3-oxo-2,5,5-trimethyl-cyclohex-1-en-1-yl)-3,7-dimethyl-nona-2,4,6,8-tetraen-1-ol which is converted into a phosphonium salt of formula VIIIAaa required for procedure (d) as described in method (d₅).

Di-nor-canthaxanthin of formula I, which can be manufactured in accordance with this invention according to procedures (a), (b), (c) and (d), can, as mentioned earlier, be reduced to di-nor-isozeaxanthin of formula IIA. The reduction is carried out according to known procedures as, for example, the use of a metal hydride or an alkyl metal hydride in an inert solvent. Suitable metal hydrides are mixed metal hydrides (e.g. lithium aluminum hydride) and non-mixed metal hydrides (e.g. diisobutylaluminum hydride). Useful solvents are, in particular, aromatic hydrocarbons such as benzene, toluene, xylene, ethylbenzene and the like.

Di-nor-canthaxanthin of formula I can, as mentioned earlier also be oxidized to di-nor-astacin (vilerythrin) of formula IIB. Selenium dioxide is a preferred oxidizing agent. Dioxane and aqueous acetic acid have also been found to be suitable. The oxidations are generally carried out in an aromatic organic solvent such as benzene and toluene. Also suitable are dioxane and aqueous acetic acid.

The resulting violerthrin of formula IIB can be reduced in a step-wise fashion. Treatment with sodium borohydride results in selective reduction of the oxo groups in the 4-position of the cyclopentene rings. Treatment with diisobutylaluminum hydride reduces the oxo groups in the 3- and 4-positions of the cyclopentene rings. In the first case there is obtained di-nor-astaxanthin [actininoerythrol] of formula IIC and in the second case there is obtained di-nor-crustaxanthin [violerythrol] of formula IID.

The polyene compounds manufactured according to the process of the present invention can be used either in the original crystalline form or in a special water-soluble form for coloring foods, pharmaceutical and cosmetic preparations.

In the crystalline form, the polyene compounds can be used principally for coloring fat-containing substances such as, for example, marzipan, suppositories and lipsticks. For coloring fat-free substances or substances having a low fat content, a water-soluble form is preferably used. This form can be produced, for example, by dissolving the particular polyene compound in an organic solvent, homogenizing the solution, optionally together with a stabilizer and a solubilizing and/or emulsifying agent, with water in the presence of a protective colloid and evaporating the emulsion formed to dryness under reduced pressure.

Especially suitable solvents are volatile halogenated hydrocarbons such as chloroform, carbon tetrachloride and methylene chloride.

Suitable stabilizers having an antioxidant activity are for example, tocopherols, 2,6-di-tert.butyl-4-hydroxy-toluene [BHT] and butyl.hydroxy-anisole [BHA].

Effective solubilizing agents are, inter alia, salts of fatty acid esters of ascorbic acid, e.g., the sodium salt of ascorbyl palmitate.

Suitable emulsifers are, for example, polyoxyethylene derivatives of sorbitol anhydrides partially esterified with fatty acids [Tweeds].

Suitable protective colloids are, inter alia, gelatins, dextrin, pectin and tragacanth.

Apart from the coloring of foods and pharmaceutical and cosmetic preparations, di-nor-canthaxanthin is also suitable for the pigmentation of egg yolks.

Surprisingly, it has been found that, although di-nor-canthaxanthin has a cherry-red color, hens fed with this compound produce eggs having deep yellow-orange pigmented egg yolks which are particularly desired by consumers in the preparation of various egg dishes.

A particular advantage in using di-nor-canthaxanthin in contrast to canthaxanthin, capsanthin/capsorubin [paprika] and citranaxanthin, the coloring materials hitherto used for egg yolk pigmenting resides in the fact that in the case of di-nor-canthaxanthin only a fraction, namely ¼ to 1/6, of the amount of the previously mentioned carotenoids is necessary in order to produce the same color effect in the egg yolks.

It will accordingly be appreciated that the invention includes within its scope a. an agent for the coloring of foods, pharmaceutical, and cosmetic preparations which contains as an essential color-imparting ingredient a polyene compound of formula III, and b. a method of imparting a color to foods, pharmaceutical, and cosmetic preparations comprising incorporating into said foods, pharmaceutical, and cosmetic preparations an effective amount of a polyene compound of formula III.

The following examples illustrate the invention.

EXAMPLE 1

0.96 g. of methyl-(3-oxo-2,5,5-trimethyl-cyclopent-1-en-1-yl)-triphenylphosphonium bromide are suspended in 40 ml. of toluene. The suspension is treated dropwise with a solution of 1 ml. of 2-N sodium methylate in methanol and, after the addition of 0.24 g. of crocetin dialdehyde, heated to boiling for 24 hours under reflux conditions. After cooling, the mixture is evaporated under reduced pressure. There is obtained all-trans di-nor-canthaxanthin [all trans 2,2'-di-nor-β-carotene-4,4'-dione] which, after purification by adsorption on silica gel, has a melting point of 233°–235°C.

The following examples illustrate the preparation of methyl-(3-oxo-2,5,5-trimethyl-cyclopent-1-en-1-yl)-triphenylphosphonium bromide.

EXAMPLE 2

124 g. of 2,4,4-trimethyl-cyclopent-2-en1-one are introduced into 67 g. of nitromethane and, after the addition of 10 ml. of a 40% solution of benzyltrimethylammonium hydroxide in methanol, stirred at 70°C. for 3 days. The mixture is then taken up in ether The ether solution is washed with 10% sulfuric acid, dried over sodium sulfate and evaporated under reduced presssure. The remaining 2,4,4-trimethyl-3-nitromethyl-cyclopentanone boils after rectification in a high vacuum at 97°–100°C/0.2 mmHg. 83 g. of the 2,4,4-trimethyl-3-nitromethyl-cyclopentanone are treated with 36 g. of sodium hydroxide in 600 ml. of water. After the addition of 300 ml. of a saturated aqueous magnesium sulfate solution, the mixture is stirred for 30 minutes, then treated dropwise at 0°C. within 1 hour with a solution of 49.7 g. of potassium permanganate in 800 ml. of water and subsequently filtered. The filtrate is extracted with methylene chloride. The extract is dried over sodium sulfate and evaporated under reduced pressure. There is obtained 1-formyl-3-oxo-2,5,5-trimethyl-cyclopentane, whose 2,4-dinitrophenylhydrazone has a melting point of 174°–177°C.

EXAMPLE 3

The 1-formyl-3-oxo-2,5,5-trimethyl-cyclopentane can alternatively be prepared according to the following method.

37 g. of 2,4,4-trimethyl-3-nitromethyl-cyclopentanone are introduced into a solution of 4.6 g. of sodium in 800 ml. of methanol and ozonolized at −70°C. After the addition of 15 ml. of dimethyl sulfate, the mixture is stirred at room temperature for 16 hours, subsequently introduced into water and extracted with ether. The ether extract is dried and evaporated under reduced pressure.

EXAMPLE 4

42 g. of 1-formyl-3-oxo-2,5,5-trimethyl-cyclopentane, prepared according to either Example 2 or 3 are heated to boiling together with 2.1 g. of p-toluenesulfonic acid, 60 g. of 2,3-dichloro-5,6-dicyano-1,4-benzoquinone and 600 ml. of toluene for 4 hours under reflux conditions. After cooling, the mixture is filtered. The filtrate is washed with an aqueous saturated sodium bicarbonate solution, dried over sodium sulfate and evaporated under reduced pressure. There is obtained crude 1-formly-3-oxo-2,5,5-trimethyl-cyclopent-1ene as an oil, whose 2,4-dinitrophenylhydrazone has a melting point of 216°–218°C. 38 g. of the crude 1-formyl-3-oxo-2,5,5-trimethyl-cyclopent-1-ene are dissolved in 1000 ml. of ethanol. The solution is treated at 0°–5°C. within 1 hour with 2.1 g. of sodium borohydride, stirred for a further 30 minutes, introduced into water and extracted with ether. The ether is dried over sodium sulfate and evaporated under reduced pressure. There is obtained 1-hydroxymethyl-3-oxo-2,5,5-trimethyl-cyclopent-1-ene which, after recrystallization from hexane, has a melting point of 38°–39°C. 8.3 g. of the 1-hydroxymethyl-3-oxo-2,5,5-trimethyl-cyclopent-1-ene are dissolved in 170 ml. of ether. After the addition of 1 ml. of pyridine, the solution is treated dropwise at 0°C. with a solution of 2.21 ml. of phosphorus tribromide in 30 ml. of ether, stirred for 1 hour, introduced into water and extracted with ether. The ether extract is dried and evaporated. The residue is taken up in 120 ml. of ethyl acetate. The solution is treated dropwise with 14.4 g. of triphenylphosphine in 120 ml. of ethyl acetate and heated to boiling for 1 hour under reflux conditions. The methyl-(3-oxo-2,5,5-trimethyl-cyclopent-1-en-1-yl-triphenylphosphonium bromide which crystallizes out in the cold has a melting point of 264°C.

EXAMPLE 5

4 g. of 1-methoxycarbonyl-3-oxo-2,5,5-trimethyl-cyclopentane are dissolved in 60 ml. of chloroform. After the addition of 10 ml. of ethane dithiol, the solution is treated with 1.5 ml. of boron trifluoride etherate, stirred for 2 hours at room temperature, introduced into water and extracted with ether. The ether extract is evaporated. The remaining 7-methoxycarbonyl-6,8,8-trimethyl-1,4-dithia-spiro[4,4]nonane is purified by adsorption on silica gel. The oil obtained has the following I.R. absorption spectrum: 1737 cm$^{-1}$[ester CO]; 1434 cm$^{-1}$[—CH$_2$—S—]; 1254 and 1173 cm$^{-1}$[ester]. 3.1 g. of the 7-methoxycarbonyl-6,8,8-trimethyl-1,4-dithiaspiro[4,4]nonane are dissolved in 30 ml. of toluene. The solution is treated at 0°C. with 28 ml. of a 1.12-M solution of diisobutylaluminum hydride in benzene, stirred for 4 hours and, after the addition of ethyl acetate, introduced into water. The organic phase is separated and evaporated. There is obtained 7-hydroxymethyl-6,8,8-trimethyl-1,4-dithia-spiro[4,4]nonane which, after recrystallization from ether/hexane, has a melting point of 72°–74°C. 2 g. of the 7-hydroxymethyl-6,8,8-trimethyl-1,4-dithia-spiro-[4,4]nonane are dissolved in 280 ml. of acetone and 14 ml of water. After the addition of 3.5 g. of cadmium carbonate and 3.5 g. of mercury (II) chloride, the solution is stirred for 24 hours at room temperature. The mixture is subsequently filtered and and the filtrate evaporated. There is obtained 1-hydroxymethyl-3-oxo-2,5,5-trimethyl-cyclopentane as an oil, whose 2,4-dinitrophenlhydrazone has a melting point of 144°–146°C. A solution of 9.5 g of pyridine in 150 ml of methylene chloride is treated with 6,0 g of chromium trioxide, stirred for 15 minutes at room temperature and, after the solution of 1.56 g of the 1-hydroxymethyl-3-oxo-2,5,5-trimethyl-cyclopentane dissolved in a small amount of methylene chloride, stirred for a further 15 minutes at room temperature. The mixture is then introduced into water and extracted with ether. The ether extract is evaporated. The remaining 1-formyl-3-oxo-2,5,5-trimethyl-cyclopentane is purified by adsorption on silica gel and converted into the desired methyl-(3-oxo-2,5,5-trimethyl-cyclopent-1-en-1-yl)-triphenylphosphonium bromide via the intermediate steps described in Example 2.

EXAMPLE 6

3.4 g. of 1-carboxy-3-oxo-2,5,5-trimethyl-cyclopentane are treated with 6 ml. of thionyl chloride. The mixture is stirred at room temperature for 2 hours and, after the addition of 2 ml. of sulfuryl chloride, stirred for a further 45 minutes and then evaporated. The remaining 1-chlorocarbonyl-3-oxo-2,5,5-trimethyl-cyclopent-1-ene is taken up in 20 ml. of methanol. After 24 hours, the solution is evaporated. The remaining, oily 1-methoxycarbonyl-3-oxo-2,5,5-trimethylcyclopent-1-ene boils at 123°–128°C/18 mmHg. 1.5 g. of 1-methoxycarbonyl-3-oxo-2,5,5-trimethyl-cyclopent-1-ene are dissolved in 10 ml of ethanol. After the additiion of 90 mg. of sodium borohydride, the mixture is stirred at room temperature for 2 hours, then introduced into water and extracted with ether. The ether extract is evaporated. The remaining 1-methoxycarbonyl-3-hydroxy-2,5,5-trimethyl-cyclopent-1-ene boils at 90°–95°C/0.2 mmHg. 3.3 g of 1-methoxycarbonyl-3-hydroxy-2,5,5-trimethyl-cyclopent-1-ene are dissolved in 70 ml. of benzene. The solution is treated at 10°C. with 35 ml. of a 1.2-M solution of diisobutylaluminum hydride in benzene, stirred for 5 hours and, after the addition of ethyl acetate, introduced into water. The organic phase is separated and evaporated. The remaining, oily 1-hydroxymethyl-3-hydroxy-2,5,5-trimethyl-cyclopent-1-ene is purified by adsorption on silica gel; I.R. spectrum: 3450 cm$^{-1}$[OH]. 3 g. of 1-hydroxymethyl-3-hydroxy-2,5,5-trimethyl-cyclopent-1-ene are dissolved in 100 ml. of methylene chloride. After the addition of 30 g. of manganese dioxide, the mixture is stirred for 24 hours and then filtered. The filtrate is evaporated. The remaining 1-formyl-3-oxo-2,5,5-trimethyl-cyclopent-1-ene is subsequently converted into the desired methyl-(3-oxo-2,5,5-trimethyl-cyclopent-1-en-1-yl)-triphenylphosphonium bromide via the intermediate steps described in Example 2.

EXAMPLE 7

3.1 g. of 1-methoxycarbonyl-3-oxo-2,5,5-trimethyl-cyclopent-1-ene are dissolved in 60 ml. of ether and 10 ml. of ethane dithiol. After the addition of 2.5 ml. of boron trifluoride etherate, the mixture is stirred for 2 months at room temperature, then introduced into water and extracted with ether. The ether extract is evaporated. The remaining, oily 7-methoxycarbonyl-6,8,8-trimethyl-1,4-dithia-spiro[4,4]non-6-ene is purified by absorption on silica gel; I.R. spectrum: 1710 cm$^{-1}$[ester CO]; 1625 cm$^{-1}$[olefin]; 1294 cm$^{-1}$[ester]. 2.8 g. of the 7-methoxycarbonyl-6,8,8-trimethyl-1,4-dithia-spiro[4,4]non-6-ene are dissolved in 30 ml. of tetrahydrofuran. After the addition of a 1.12-M solution of diisobutylaluminum hydride in benzene, the solution is stirred for 3 hours at 0°C. After dilution with 15 ml. of ethyl acetate, the mixture is introduced into water and extracted with ether. The ether extract is evaporated. There is obtained 7-hydroxymethyl-6,8,8-trimethyl-1,4-dithiaspior[4,4]non-6-ene which, after recrystallization from ethyl acetate, has a melting point of 59°C. 0.5 g. of the 7-hydroxymethyl-6,8,8-trimethyl-1,4-dithia-spiro[4,4]non-6-ene are dissolved in 5 ml. of acetone and 2 ml. of water. After the addition of 700 mg. of cadmium carbonate and 650 mg. of mercury (II) chloride, the mixture is stirred for 24 hours, then introduced into water and extracted with ether. The ether extract is evaporated. The 1-hydroxymethyl-3-oxo-2,5,5-trimethyl-cyclopent-1-ene formed is subsequently converted into the desired methyl-(3-oxo-2,5,5-trimethylcyclopent-1-en-1-yl)-triphenylphosphonium bromide via the intermediate steps described in Example 2.

EXAMPLE 8

6.85 g. of 5-(3-oxo-2,5,5-trimethyl-cyclopent-1-en-1-yl)-3-methyl-penta-2,4-diene-1-triphenylphosphonium bromide and 0.78 g of 2,7-dimethyl-octa-2,6-dien-4-yne-1,8-dial are dissolved in 70 ml. of ethanol. To the resulting solution there are added dropwise at 0°C. 6.25 ml. of a 2-N sodium methylate solution in methanol. The mixture is stirred for 1 hour at 0°C., then for 1 hour at room temperature and finally for 1 hour at 70°C. After cooling, the mixture is introduced into water and extracted with chloroform. The residue remaining after evaporation of the chloroform extract is taken up in 70 ml. of methanol/water (80:20). The solution is heated to boiling for 2 hours under reflux conditions. The 15,15'-dehydro-di-nor-canthaxanthin [2,2'-di-nor-15,15'-dehydro-β-carotene-4,4'-dione] which precipitates in the cold, has a melting point of 220°C. 1.98 g.

of the 15,15'-dehydro-di-nor-canthaxanthin are dissolved in 75 ml. of methylene chloride and 50 ml. of methanol. After the addition of 0.5 ml. of triethylamine, the solution is hydrogenated in the presence of a partially inactivated palladium catalyst at room temperature and atmospheric pressure until 1 mole equivalent of hydrogen has been taken up. The catalyst is filtered off and the solution evaporated. The remaining all-trans di-nor-canthaxanthin has a melting point of 233°–235°C.

EXAMPLE 9

5-(3-oxo-2,5,5-trimethyl-cyclopent-1-en-1-yl)-3-methyl-penta-2,4-diene-1-triphenylphosphonium bromide is prepared according to the following method. 10 g. of 1-hydroxymethyl-3-oxo-2,5,5-trimethyl-cyclopent-1-ene are dissolved in 200 ml. of ether. After the addition of 1.2 ml. of pyridine, the solution is treated dropwise at −20°C. with a solution of 2.9 ml. of phosphorus tribromide in 40 ml. of ether, stirred for 1 hour, introduced into water and then extracted with ether. The ether extract is evaporated. The remaining 1-bromomethyl-3-oxo-2,5,5-trimethyl-cyclopent-1-ene is taken up in dimethylformamide. After the addition of 11.5 g. of sodium phenylsulfinate, the mixture is stirred at room temperature for 90 minutes, then introduced into water and extracted with ether. After evaporation of the ether extract, there is obtained methyl-(3-oxo-2,5,5-trimethylcyclopent-1-en-1-yl)-phenylsulfone of melting point 116°–118°C. 23.5 g. of the methyl-(3-oxo-2,5,5-trimethyl-cyclopent-1-en-1-yl)-phenylsulfone are dissolved in 60 ml. of dimethylformamide. After the addition of 23 g. of potassium tert.butylate, the mixture is stirred at 0°C. for 30 minutes and then treated dropwise with 25 g. of 1-acetoxy-4-chloro-3-methyl-but-2-ene dissolved in 50 ml. of dimethylformamide. The mixture is stirred at room temperature for 16 hours, then introduced into water and extracted with ethyl acetate. The organic phase is separated and evaporated. The residue is taken up in methanol. After the addition of 45 g. of potassium carbonate in 150 ml. of water, the mixture is stirred for 2 hours, then introduced into water and extracted with ethyl acetate. After evaporation of the extract, there is obtained 5-(3-oxo-2,5,5-trimethyl-cyclopent-1-en1-yl)-5-phenylsulfonyl3-methyl-pent-2-en-1-ol which, after recrystallization from hexane, has a melting point of 149°–153°C. 17.6 g. of the 5-(3-oxo-2,5,5-trimethyl-cyclopent-1-en-1-yl)-5-phenylsulfonyl-3-methyl-pent-2-en-1-ol are dissolved in 1000 ml of methylene chloride. After the addition of 300 g. of manganese dioxide, the mixture is stirred for 16 hours and then filtered. After evaporation of the filtrate, there is obtained 5-(3-oxo-2,5,5-trimethyl-cyclopent-1-en-1-yl)-5-phenylsulfonyl-3-methyl-pent-2-en-1-al which, after recrystallization from ether, has a melting point of 132°–134°C. 16.4 g. of the 5-(3-oxo-2,5,5-trimethyl-cyclopent-1-en-1-yl)-5-phenylsulfonyl-3-methyl-pent-2-en-1-al are dissolved in 300 ml. of tetrahydrofuran and 300 ml. of isopropanol. The solution is treated dropwise at 0°C. with 5 ml. of a 50% aqueous potassium hydroxide solution. The mixture is stirred for 1 hour, then introduced into water and extracted with ether. After evaporation of the ether extract, there is obtained 5-(3-oxo-2,5,5-trimethylcyclopent-1-en1-yl)-3-methyl-penta-2,4-dien-1-al which, after recrystallization from methylene chloride/hexane (1:1), has a melting point of 91°–93°C. 6.4 g. of the 5-(3-oxo- 2,5,5-trimethyl-cyclopent-1-en-1-yl)-3-methyl-penta-2,4-dien-1-al are dissolved in 120 ml. of ethanol. After the addition of 285 mg. of sodium borohydride, the mixture is stirred at 0°C. for 90 minutes. The mixture is then introduced into water and extracted with ether. After evaporation of the ether extract, there is obtained 5-(3-oxo-2,5,5-trimethyl-cyclopent-1-en-1-yl)-3-methyl-penta-2,4-dien-1-ol which, after recrystallization from ether, has a melting point of 116°–118°C. 5 g. of the 5-(3-oxo-2,5,5-trimethyl-cyclopent-1-en-1-yl)-3-methyl-penta-2,4-dien-1-ol are dissolved in 20 ml. of methylene chloride and 3 ml. of dimethylformamide. The solution is treated dropwise at −20°C. with 2 ml. of phosphorus tribromide. The mixture is stirred for 1 hour at 0°C., then introduced into water and extracted with ether. The ether extract is evaporated. The remaining 1-bromo-5-(3-oxo-2,5,5-trimethyl-cyclopent-1-en-1-yl)-3-methyl-penta-2,4-diene is dissolved in ethyl acetate. The solution is treated dropwise with 7 g. of triphenylphosphine in 40 ml. of ethyl acetate, stirred for 2 hours and then filtered. The filtrate is evaporated. There is obtained 5-(3-oxo-2,5,5-trimethyl-cyclopent-1-en-1-yl)-3-methyl-penta-2,4-diene-1-triphenylphosphonium bromide; I.R. spectrum: $1690^{cm-1}$ [ketone]; 742, 723, $690^{cm-1}$ [mono-substituted benzene].

EXAMPLE 10

80 g. of 2,7-dimethyl-octa-2,6-dien-yne-1,8-bis-triphenylphosphonium bromide are introduced in the course of 30 minutes into a solution of 0,22 mol. of phenyl lithium in 300 ml. of ether. The mixture is then treated dropwise with a solution of 5-(3-oxo-2,5,5-trimethyl-cyclopent-1-en-1-yl)-3-methyl-penta-2,4-dien-1-al in 200 ml. of ether. The mixture is heated to boiling for 16 hours under reflux conditions and, after cooling, then evaporated. The residue is washed with aqueous methanol to yield 15,15'-dehydro-di-nor-canthaxanthin [2,2'-di-nor-15,15'-dehydro-β-carotene-4,4'-dione] of melting point 220°C, which is converted into di-nor-canthaxanthin as described in Example 8; melting point 233°–235°C.

EXAMPLE 11

5-(3-oxo-2,5,5-trimethyl-cyclopent-1-en-1-yl)-3-methyl-penta-2,4-dien-1-al can be prepared as described in Example 9 or also in accordance with the following method.

2.8 g. of the 1-formyl-3-oxo-2,5,5-trimethyl-cyclopentane are dissolved in 200 ml. of isopropanol. The solution is treated first with 6.4 g. of 1,1-diethoxy-3-methyl-but-2-ene-4-triphenylphosphonium bromide and then with 1.5 ml. of a 50% aqueous potassium hydroxide solution. The mixture is stirred for 2 hours and, after the dropwise addition of 15 ml. of 2-N sulfuric acid, introduced into water and extracted with ether. After evaporation of the the ether extract, there is obtained 5-(3-oxo-2,5,5-trimethyl-cyclopent-1-yl)-3-methyl-penta-2,4-dien-1-al as an oil; I.R. spectrum: 1750 $cm^{-1}$ [ketone]; 1670 $cm^{-1}$ [aldehyde].

2 g. of the 5-(3-oxo-2,5,5-trimethyl-cyclopent-1-yl)-3-methyl-penta-2,4-dien-1-al, 50 mg. of p-toluenesulfonic acid, 2.5 g. of 2,3-dichloro-5,6-dicyano-1,4-benzoquinone and 40 ml. of toluene was heated to boiling for 5 hours under reflux conditions. After cooling, the mixture is filtered. After evaporation of the filtrate, there is obtained 5-(3-oxo-2,5,5-trimethyl-cyclopent-1-en-1-yl)-3-methyl-penta-2,4-dien-1-al which, after pu-

EXAMPLE 12

A mixture of 5.72 g. of all-trans 9-(3-oxo-2,5,5-trimethyl-cyclopent-1-en-1-yl)3,7-dimethyl-nona-2,4,6,8-tetraen-1-ol, 5.76 g. of triphenylphosphine, 2.16 g. of sulfuric acid and 100 ml. of methanol is stirred for 20 hours. After the addition of 2.7 ml. of a 50% aqueous potassium hydroxide solution, the mixture is treated with 6.5 g. of all-trans 9-(3-oxo-2,5,5-trimethyl-cyclopent-1-en-1-yl)-3,7-dimethyl-nona-2,4,6,8-tetraen-1-al. The mixture is stirred for 4 hours, then introduced into water and extracted with chloroform. The chloroform extract is evaporated and the residue obtained heated to boiling in methanol/water (80:20) for 20 hours under reflux conditions. By cooling, there is precipitated all-trans di-nor-canthaxanthin [2,2'-di-nor-β-carotene-4,4'-dione] which, after recrystallization from chloroform/hexane, has a melting point of 233°–235°C.

EXAMPLE 13

All-trans 9-(3-oxo-2,5,5-trimethyl-cyclopent-1-en-1-yl)-3,7-dimethyl-nona-2,4,6,8-tetraen-1-al can be prepared according to the following method.

1.8 g. of the 1-hydroxymethyl-3-oxo-2,5,5-trimethyl-cyclopent-1-ene are dissolved in 30 ml. of ether. After the addition of 0.2 ml. of pyridine, the solution is treated dropwise at —20°C. with a solution of 0.3 ml. of phosphorus tribromide in 5 ml. of ether. The mixture is stirred for 1 hour, then introduced into water and extracted with ether. The ether extract is evaporated. The remaining 1-bromomethyl-3-oxo-2,5,5-trimethyl-cyclopent-1-ene is taken up in 10 ml. of dimethylformamide. After the addition of 2 gram equivalents of potassium tert.butylate, the mixture is stirred for 30 minutes at 0°C., treated with 3.5 g. of 8-(p-tolylsulphonyl)-3,7-dimethyl-octa-2,4,6-trien-1-al, stirred for 16 hours at room temperature, introduced into water and then extracted with ether. After evaporation of the ether extract, there is obtained 9-(3-oxo-2,5,5-trimethyl-cyclopent-1-en-1-yl)-3,7-dimethyl-nona-2,4,6,8-tetraen-1-al which, after purification by adsorption on silica gel, has a mass spectrum m/e of 284.

EXAMPLE 14

8-(p-tolylsulfonyl)-3,7-dimethyl-octa-2,4,6-trien-1-al used as the condensation component in the foregoing Example, can be prepared according to the following method.

12.8 g. of 1-ethoxycarbonyl-6-hydroxymethyl-2-methyl-hepta-1,3,5-triene are dissolved in 40 ml. of methylene chloride. The solution is treated dropwise at —20°C. with a solution of 5.5 ml. of phosphorus tribromide in 40 ml. of methylene chloride. After 2 hours, the mixture is introduced into water and extracted with ether. The ether extract is evaporated. The remaining bromide is taken up in 140 ml. of dimethylformamide. The solution is subsequently treated with 15 g. of sodium p-tolylsulphinate, stirred for 2 hours and then introduced into water. There precipitates 1-ethoxycarbonyl-7-(p-tolylsulfonyl)-2,6-dimethyl-hepta-1,3,5-triene which, after recrystallization from ethyl acetate, has a melting point of 154°–156°C. 16.8 g. of the 1-ethoxycarbonyl-7-(p-tolylsulfonyl)-2,6-dimethyl-hepta-1,3,5-triene are dissolved in 600 ml. of tetrahydrofuran. After the dropwise addition of 110 ml. of a 1.12-M solution of diisobutylaluminum hydride in hexane, the solution is stirred for 2 hours at —20°C. The mixture is then diluted with methanol, treated dropwise with 2-N hydrochloric acid, introduced into water and extracted with ether. After evaporation of the ether extract, there is obtained 1-hydroxymethyl-7-(p-tolylsulfonyl)-2,6-dimethyl-hepta-1,3,5-triene which, after recrystallization from methylene chloride, has a melting point of 129°–131°C. 14.6 g. of 1-hydroxymethyl-7-(p-tolylsulfonyl)-2,6-dimethyl-hepta-1,3,5,-triene are dissolved in 700 ml. of methylene chloride. After the addition of 250 g. of manganese dioxide, the mixture is stirred at room temperature for 8 hours and then filtered. After evaporation of the filtrate, there is obtained 8-(p-tolylsulfonyl)-3,7-dimethyl-octa-2,4,6-trien-1-al which, after recrystallization from methylene chloride/hexane, has a melting point of 140°–142°C. This compound is then condensed with 1-bromomethyl-3-oxo-2,5,5-trimethyl-cyclopent-1-ene as previously described to form 9-(3-oxo-2,5,5-trimethyl-cyclopent-1-en-1-yl)-3,7-dimethyl-nona-2,4,6,8-tetraen-1-al.

EXAMPLE 15

5 g. of 5-(3-oxo-2,5,5-trimethyl-cyclopent-1-en-1-yl)-5-phenylsulfonyl-3-methyl-pent-2-en-1-ol are dissolved in 200 ml. of toluene. After the addition of 0.5 ml. of pyridine, the solution is treated dropwise at 0°C. with 0.7 ml. of phosphorus tribromide and then stirred for 2 hours. The mixture is subsequently introduced into water and extracted with toluene. The toluene phase is concentrated to 100 ml., treated with 4 g. of triphenylphosphine and stirred for 24 hours at 60°C. The 5-(3-oxo-2,5,5-trimethyl-cyclopent-1-en-1-yl)-5-phenylsulfonyl-3-methyl-pent-2-ene-1-triphenylphosphonium bromide which crystallizes in the cold, has a melting point of 107°–110°C. 0.7 g. of the 5-(3-oxo-2,5,5-trimethyl-cyclopent-1-en-1-yl)-5-phenylsulfonyl-3-methyl-pent-2-ene-1-triphenylphosphonium bromide are dissolved in 25 ml. of tetrahydrofuran. The solution is treated dropwise at 0°C. with 1 ml. of 2-N sodium methylate in methanol, stirred for 10 minutes and, after the addition of 150 mg. of 1-acetoxy-3-methyl-but-2-en-4-al, stirred for a further 20 hours. The mixture is then introduced into water and extracted with ether. The ether extract is evaporated. There is obtained all-trans 9-(3-oxo-2,5,5-trimethyl-cyclopent-1-en-1-yl)-3,7-dimethyl-nona-2,4,6,8-tetraen-1-ol which has a mass spectrum m/e of 286. This compound is purified by adsorption on silica gel.

2 g. of the all-trans 9-(3-oxo-2,5,5-trimethyl-cyclopent-1-en-1-yl)-3,7-dimethyl-nona-2,4,6,8-tetraen-1-ol are then dissolved in 100 ml. of methylene chloride. After the addition of 20 g. of manganese dioxide, the mixture is stirred for 24 hours and then filtered. After evaporation of the filtrate, there is obtained 9-(3-oxo-2,5,5-trimethyl-cyclopent-1-en-1-yl)-3,7-dimethyl-nona-2,4,6,8-tetraen-1-al which has a mass spectrum m/e of 284.

EXAMPLE 16

4.6 g. of 5-(3-oxo-2,5,5-trimethyl-cyclopent-1-en-1-yl)-5-phenylsulfonyl-3-methyl-pent-2-en-1-al and 9 g. of 1,1-diethoxy-3-methyl-but-2-ene-4-triphenylphosphonium bromide are dissolved in 100 ml. of isopropanol. The mixture is treated dropwise at —30°C. with 3.5 ml. of a 50% aqueous potassium hydroxide solution, stirred for 1 hour and, after the addition of 10 ml. of 5-N sulfuric acid, stirred for a further 20 minutes. After the addition of 5 ml. of 50% potassium hydroxide solution, the mixture is introduced into water and extracted with ether. After evaporation of the ether extract, there is obtained all-trans 9-(3-oxo-2,5,5-trimethyl-cyclopent-1-en-1-yl)-3,7-dimethyl-nona-2,4,6,8-tetraen-1-al.

EXAMPLE 17

2.18 g. of 5-(3-oxo-2,5,5-trimethyl-cyclopent-1-en-1-yl)-3-methyl-penta-2,4-dien-1-al are dissolved in 100 ml. of isopropanol. The solution is treated first with 5 g. of 1,1-diethoxy-3-methyl-but-2-ene-4-triphenylphosphonium bromide and then with 1.2 ml. of a 50% aqueous potassium hydroxide solution. The mixture is stirred for 1 hour and, after the dropwise addition of 10 ml. of 2-N sulfuric acid, then introduced into water and extracted with ether. After evaporation of the ether extract, there is obtained all-trans 9-(3-oxo-2,5,5-trimethyl-cyclopent-1-en-1-yl)-3,7-dimethyl-nona-2,4,6,8-tetraen-1-al.

EXAMPLE 18

9-(3-oxo-2,5,5-trimethyl-cyclopent-1-en-1-yl)-3,7-dimethyl-nona-2,4,6,8-tetraen-1-ol can also be prepared from the corresponding aldehyde. 1 g. of all-trans 9-(3-oxo-2,5,5-trimethyl-cyclopent-1-en-1-yl)-3,7-dimethyl-nona-2,4,6,8-tetraen-1-al are dissolved in 80 ml. of ethanol. The solution is treated with 1 mole equivalent of sodium borohydride, stirred for 1 hour at room temperature, then introduced into water and extracted with ether. After evaporation of the ether extract, there is obtained all-trans 9-(3-oxo-2,5,5-trimethyl-cyclopent-1-en-1-yl)-3,7-dimethyl-nona-2,4,6,8-tetraen-1-ol, which can be converted into the phosphonium sulfate and subsequently condensed as described hereinbefore.

EXAMPLE 19

0.28 g. of all-trans di-nor-canthaxanthin are dissolved in 30 ml. of toluene. The solution is treated with 1.5 ml. of a 1.12-M solution of diisobutylaluminum hydride in benzene and stirred for 1 hour. The mixture is then introduced into water and extracted with benzene. After evaporation of the benzene extract, there is obtained di-nor-isozexanthin [2,2-di-nor-β-carotene-4,4'-diol] which, after recrystallization from ether/hexane, has a melting point of 163°–165°C.

EXAMPLE 20

0.3 g. of all-trans di-nor-canthaxanthin are dissolved in 50 ml. of toluene. After the addition of 10.2 g. of selenium dioxide and 0.7 ml. of water, the mixture is heated to boiling for 16 hours under reflux conditions. The mixture is then introduced into water and extracted with toluene. After evaporation of the toluene extract, there is obtained di-nor-astacin [2,2'-di-nor-β-carotene-3,3',4,4'-tetraone; violerythrin] which, after recrystallization by adsorption on silica gel, has a mass spectrum m/e of 564.

The following examples illustrate typical coloring agents provided by this invention and their application.

EXAMPLE 21

A food coloring preparation is prepared according to the following method.

1.0 g. of di-nor-canthaxanthin, 0.1 g. of d,1-α-tocopherol, 0.4 g. of arachis oil and 1.0 g. of ascorbyl palmitate are dissolved in 50 ml. of hot chloroform. The solution is homogenized with 5.0 g. of gelatine, 2.5 g. of sugar and 0.2 g. of sodium carbonate dissolved in 50 ml. of water. The homogenate is poured onto a plate, dried in vacuo until free of chloroform and triturated.

EXAMPLE 22

10–100 g. of the coloring preparation obtained according to Example 20 are dissolved in 100–1000 ml. of warm water. The solution is added to 100 kg of bonbon mass, either towards the end of the cooking process or during the addition of aromas succeeding same. There is obtained a scarlet-colored bonbon mass, which can be treated with stawberry, redcurrent and/or raspberry aromas.

EXAMPLE 23

200 mg. of the coloring preparation obtained according to Example 20, containing 20 mg. of di-nor-canthaxanthin, are added to that amount of pudding powder required for 1 liter of ready-prepared pudding. The pudding mass obtained after the usual preparation (mixing, possible boiling up with milk) is cherry-red.

EXAMPLE 24

200 mg. of the coloring preparation obtained according to Example 20, containing 20 mg. of di-nor-canthaxanthin, are dissolved in 5 ml. of warm water. The solution is mixed with those ingredients required for 1 liter of ice-cream (cream, milk, sugar, gelatine, aromas). There is obtained a strawberry-red ice-cream.

We claim:
1. A compound of the formula:

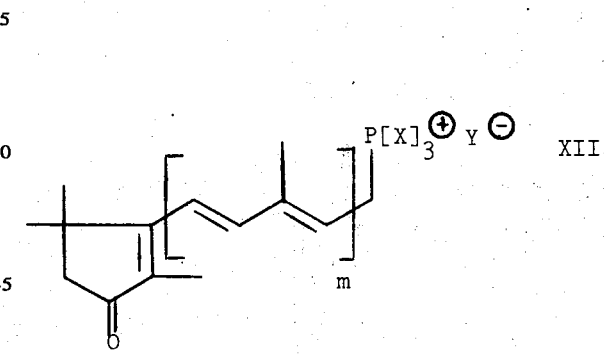

wherein X is an aryl group and Y is an anion of an acid selected from the group consisting of Cl⁻, Br⁻, $R_9COO^-$, wherein $R_9$ is lower alkyl or phenyl; m is zero or 1.

2. A compound according to claim 1 wherein said compound is methyl-(3-oxo-2,5,5-trimethyl-cyclopent-1-en-1-yl)-triphenylphosphonium bromide.

3. A compound according to claim 1 wherein said compound is 5-(3-oxo-2,5,5-trimethyl-cyclopent-1-en-1-yl)-3-methyl-penta-2,4-diene-1-triphenylphosphonium bromide.

4. A compound according to claim 1 wherein said compound is 9-(3-oxo-2,5,5-trimethyl-cyclopent-1-en-1-yl)-3,7-dimethyl-nona-2,4,6,8-tetraene-1-triphenylphosphonium bromide.

* * * * *